(12) United States Patent
Weichert et al.

(10) Patent No.: US 6,291,502 B1
(45) Date of Patent: Sep. 18, 2001

(54) USE OF 2-IMIDAZOLYL-SUBSTITUTED CARBINOLS FOR THE PRODUCTION OF A MEDICAMENT FOR THE TREATMENT OR PHOPHYLAXIS OF DISEASES CAUSED BY ISCHEMIC CONDITIONS

(75) Inventors: Andreas Weichert, Egelsbach; Udo Albus, Florstadt; Hans-Willi Jansen, Niedernhausen, all of (DE)

(73) Assignee: Aventis Pharma Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 09/695,920

(22) Filed: Oct. 26, 2000

(30) Foreign Application Priority Data

Oct. 27, 1999 (DE) .............................. 199 51 701

(51) Int. Cl.$^7$ ................................. A61K 31/415
(52) U.S. Cl. ................................................. 514/400
(58) Field of Search .............................. 514/400

(56) References Cited

U.S. PATENT DOCUMENTS

| | | | |
|---|---|---|---|
| 4,152,441 | 5/1979 | Van der Stelt . | |
| 4,213,994 | 7/1980 | Gebert et al. . | |
| 5,736,554 | * | 4/1998 | Spada et al. .................. 514/303 |
| 6,175,013 | * | 1/2001 | Hipskind et al. ................. 514/400 |

FOREIGN PATENT DOCUMENTS

WO 97/49704   12/1997   (WO) .

OTHER PUBLICATIONS

Marpat Abstract of JP 63270665 A2, "Preparation of Imidazole Derivatives as Antiulcer Agents." Toyofuku et al.
Derwent Abstract of JP 63270665 A, "New Aralkyl Oxy Methyl Imidazole Derivs.–useful as Antiulcer Agents."

* cited by examiner

Primary Examiner—James H. Reamer
(74) Attorney, Agent, or Firm—Finnegan, Henderson, Farabow, Garrett & Dunner, L.L.P.

(57) ABSTRACT

Methods of using 2-imidazolyl-substituted carbinols of the formula I for treating or preventing diseases caused by ischemic conditions:

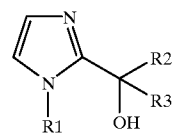

I

In these carbinols, R1, R2 and R3 have the meanings indicated in the specification and claims.

9 Claims, No Drawings

USE OF 2-IMIDAZOLYL-SUBSTITUTED CARBINOLS FOR THE PRODUCTION OF A MEDICAMENT FOR THE TREATMENT OR PHOPHYLAXIS OF DISEASES CAUSED BY ISCHEMIC CONDITIONS

This application claims benefit under 35 U.S.C. §119 of application no. 19951701.0, filed on Oct. 27, 1999 in Germany, which is incorporated in its entirety by reference herein.

Recently, patent applications have been published which claim compounds having the formula I:

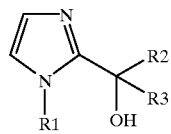

DE-A 23 05 212 describes compounds of similar constitution having analgesic, anorectic, antiinflammatory and antipyretic activity. DE-A-2164919 claims the anticholesteremic action of these compounds. WO 97 49 704 describes representatives of this class of compound in the indication carcinomatous diseases, where they intervene in vitamin A acid metabolism. JP 63270665 describes their anti-ulcer activity.

A reference to an action of these compounds in ischemic conditions is not found in any of these publications.

The invention relates to the use of 2-imidazole-substituted carbinols I and of their pharmaceutically tolerable salts in which:

R1 is straight-chain or branched $C_1$–$C_8$-alkyl or phenyl-$(CH_2)_m$—;
m is zero, 1 or 2;
where the phenyl nucleus is unsubstituted or carries one to three substituents selected from the group consisting of F, Cl, $CH_3$ and $CH_3O$, R2 and R3
are straight-chain or branched $C_1$–$C_6$-alkyl or phenyl, where the phenyl nucleus is unsubstituted or carries one to three substituents selected from the group consisting of F, Cl, $CH_3$ and $CH_3O$;

or

R2 and R3
can together form a ($C_5$–$C_6$) ring,
which is unsubstituted or to which phenyl rings are fused for the production of a medicament for the therapy or prophylaxis of ischemic conditions.

Preferred compounds I used are those in which:
R1 is straight-chain or branched $C_4$–$C_6$-alkyl, phenyl or benzyl,
where the phenyl nucleus is unsubstituted or carries one to three substituents selected from the group consisting of F, Cl, $CH_3$ and $CH_3O$;

R2 and R3
are straight-chain or branched $C_1$–$C_6$-alkyl or phenyl, where the phenyl nucleus is unsubstituted or carries one to three substituents selected from the group consisting of F, Cl, $CH_3$ and $CH_3O$;

or

R2 and R3
together with the carbon atom to which they are bonded, form a fluorene.

If one of the three substituents R1, R2 or R3 contains an asymmetric center, the invention includes both compounds of S and R configuration. The compounds used according to the invention can be present as optical isomers, as diastereoisomers, as racemates or as mixtures thereof.

Surprisingly, these already known compounds are distinguished by inhibition of $Na^+/H^+$ exchange. Thus, on account of their pharmacological properties, they are outstandingly suitable as antiarrhythmic pharmaceuticals having a cardioprotective component for infarct prophylaxis and infarct treatment and also for the treatment of angina pectoris, where they also preventively inhibit or greatly decrease the pathophysiological processes in the formation of ischemically induced damage, in particular in the elicitation of ischemically induced cardiac arrhythmias. Because of their protective actions against pathological hypoxic and ischemic situations, the compounds of the formula I, on account of inhibition of the cellular $Na^+/H^+$ exchange mechanism, can be used as pharmaceuticals for the treatment of all acute or chronic damage caused by ischemia or diseases primarily or secondarily induced thereby. This relates to their use as pharmaceuticals for surgical interventions, e.g. in organ transplantation, where the compounds can be used both for the protection of the organs in the donor before and during removal, for the protection of removed organs, for example during treatment with or storage thereof in physiological bath fluids, and during transfer to the recipient's body. The compounds are also valuable pharmaceuticals having a protective action when carrying out angioplastic surgical interventions, for example on the heart and on peripheral vessels. According to their protective action against ischemically induced damage, the compounds used according to the invention are also suitable as pharmaceuticals for the treatment of ischemias of the nervous system, in particular of the central nervous system, where they are suitable, for example, for the treatment of stroke or of cerebral edema. Moreover, the compounds of the formula I are also suitable for the treatment of forms of shock, such as, for example, of allergic, cardiogenic, hypovolemic and of bacterial shock.

The compounds used according to the invention are efficacious inhibitors of the cellular sodium/proton antiporter ($Na^+/H^+$ exchanger), which is raised in numerous diseases (essential hypertension, atherosclerosis, diabetes etc.) even in those cells which are easily accessible to measurements, such as, for example, in erythrocytes, platelets or leukocytes. The compounds according to the invention are therefore suitable as outstanding and simple scientific tools, for example in their use as diagnostics for the determination and differentiation of certain forms of hypertension, but also of atherosclerosis, of diabetes, etc. Moreover, the compounds of the formula I are suitable for preventive therapy for the prevention of the genesis of high blood pressure, for example of essential hypertension.

Pharmaceuticals which contain a compound I can in this case be administered orally, parenterally, intravenously, rectally or by inhalation, the preferred administration being dependent on the particular course of the disease. The compounds I can in this case be used on their own or together with pharmaceutical excipients, namely both in veterinary and in human medicine.

The person skilled in the art is familiar on the basis of his/her expert knowledge with those excipients which are suitable for the desired pharmaceutical formulation. In addition to solvents, gel-forming agents, suppository bases, tablet excipients, and other active compound carriers, it is possible to use, for example, antioxidants, dispersants, emulsifiers, antifoams, flavor corrigents, preservatives, solubilizers or colorants.

For an oral administration form, the active compounds I are mixed with the additives suitable therefor, such as vehicles, stabilizers or inert diluents, and brought by the customary methods into the suitable administration forms, such as tablets, coated tablets, hard gelatin capsules, aqueous, alcoholic or oily solutions. Inert carriers which can be used are, for example, gum arabic, magnesia, magnesium carbonate, potassium phosphate, lactose, glucose or starch, in particular corn starch. In this case, preparation can be carried out both as dry and as moist granules. Possible oily vehicles or solvents are, for example, vegetable or animal oils, such as sunflower oil or cod-liver oil.

For subcutaneous or intravenous administration, the active compounds I, if desired with the substances customary therefor such as solubilizers, emulsifiers or further excipients, are brought into solution, suspension or emulsion. Suitable solvents are, for example: water, physiological saline solution or alcohols, e.g. ethanol, propanol, glycerol, in addition also sugar solutions such as glucose or mannitol solutions, or alternatively a mixture of the various solvents mentioned.

A suitable pharmaceutical formulation for administration in the form of aerosols or sprays is, for example, solutions, suspensions or emulsions of the active compound of the formula I used according to the invention in a pharmaceutically acceptable solvent, such as, in particular, ethanol or water, or a mixture of such solvents.

If required, the formulation can also contain still other pharmaceutical excipients such as surfactants, emulsifiers and stabilizers and also a propellant. Such a preparation contains the active compound customarily in a concentration from approximately 0.1 to 10, in particular from approximately 0.3 to 3, % by weight.

The dose of the active compound of the formula I to be administered and the frequency of administration depend on the potency and duration of action of the compounds used; moreover also on the nature and severity of the disease to be treated and on the sex, age, weight and individual responsiveness of the mammal to be treated.

On average, the daily dose of a compound of the formula I in the case of a patient weighing approximately 75 kg is at least 0.001 mg/kg, preferably 0.01 mg/kg, to at most 10 mg/kg, preferably 1 mg/kg, of body weight. In acute episodes of the disease, for example immediately after suffering a cardiac infarct, even higher and especially more frequent doses may also be necessary, e.g. up to 4 individual doses per day. In particular in the case of i.v. administration, for example in the case of an infarct patient in the intensive care unit, up to 200 mg per day may be necessary.

EXPERIMENTAL SECTION

List of Abbreviations:

| RT | room temperture |
| EA | ethyl acetate (EtOAc) |
| m.p. | melting point |
| THF | tetrahydrofuran |
| eq. | equivalent |

EXAMPLE 1

9-(1-Benzyl-1H-imidazol-2-yl)-9H-fluoren-9-ol, colorless solid, m.p. 149° C., M++H=339.

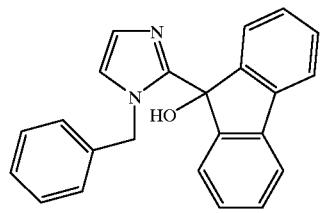

1.2 eq of n-butyllithium are added at −70° C. to N-benzylimidazole in THF. The mixture is allowed to warm to −20° C. in the course of one hour and is then again cooled to −70° C. After addition of 1 eq of fluorenone in THF, it is allowed to warm to RT in the course of 5 h. Aqueous work-up, extraction with EA, followed by subsequent drying of the organic phase over magnesium sulfate and evaporation of the solvents yields a solid, yellowish residue. Trituration with diethyl ether yields a solid, which is filtered off with suction.

EXAMPLE 2

(1-Butyl-1H-imidazol-2-yl)phenyl-4-fluorophenylcarbinol, colorless solid, m.p. 138° C., M++H=325.

Procedure as described in 1), only using N-n-butylimidazole and 4-fluorophenyl phenyl ketone.

Pharmacological Data:

Inhibition of the Na+/H+ Exchanger of Rabbit Erythrocytes

White New Zealand rabbits (Ivanovas) received a standard diet with 2% cholesterol for six weeks in order to activate the Na+/H+ exchange and thus to be able to determine the Na+ influx into the erythrocytes via Na+/H+ exchange by flame photometry. The blood was taken from the auricular arteries and rendered incoagulable by means of 25 IU of potassium heparin. A part of each sample was used for the duplicate determination of the hematocrit by centrifugation. Aliquots of 100 µl in each case served for the measurement of the Na+ starting content of the erythrocytes.

In order to determine the amiloride-sensitive sodium influx, 100 µl of each blood sample were incubated in 5 ml in each case of a hyperosmolar salt/sucrose medium (mmol/l: 140 NaCl, 3 KCl, 150 sucrose, 0.1 ouabain, 20 trishydroxymethylaminomethane) at pH 7.4 and 37° C. The erythrocytes were then washed three times with ice-cold $MgCl_2$/ouabain solution (mmol/l: 112 $MgCl_2$, 0.1 ouabain) and hemolyzed in 2.0 ml of distilled water. The intracellular sodium content was determined by flame photometry.

The Na+ net influx was calculated from the difference between sodium starting values and the sodium content of the erythrocytes after incubation. The amiloride-inhibitable sodium influx followed from the difference in the sodium content of the erythrocytes after incubation with and without amiloride 3×10⁻⁴ mol/l. This procedure was also used in the case of the compounds according to the invention.

Results
Inhibition of the Na⁺/H⁺ Exchanger:

| Example | IC$_{50}$ ($\mu$mol/l) |
|---------|------------------------|
| 1:      | 9.3                    |
| 2:      | <50                    |

We claim:
1. A method of treating or preventing a disease caused by ischemic conditions, comprising administering to a host in need thereof an effective amount of a compound I

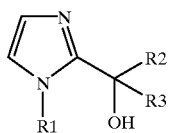

in which:
R1 is straight-chain or branched C$_1$–C$_8$-alkyl or phenyl-(CH$_2$)$_m$—;
m is zero, 1 or 2,
where the phenyl nucleus is unsubstituted or carries one to three substituents selected from the group consisting of F, Cl, CH$_3$ and CH$_3$O,
R2 and R3
are straight-chain or branched C$_1$–C$_6$-alkyl or phenyl, where the phenyl nucleus is unsubstituted or carries one to three substituents from the groups F, Cl, CH$_3$ or CH$_3$O;
or
R2 and R3
can together form a (C$_5$–C$_6$) ring, which is unsubstituted or to which phenyl rings are fused,
or of a pharmaceutically tolerable salt thereof.
2. A method of claim 1, wherein the disease is cardiac infarct.
3. A method of claim 1, wherein the disease is angina pectoris.
4. A method of claim 1, wherein the ischemic conditions are of the heart.
5. A method of claim 1, wherein the ischemic conditions are of the peripheral and central nervous system and of stroke.
6. A method of claim 1, wherein the ischemic conditions are of the peripheral organs and limbs.
7. A method of claim 1, wherein the treatment is of states of shock.
8. A method of protecting a transplant organ during surgical operations and organ transplantations, comprising administering to a host in need thereof an effective amount of of a compound I

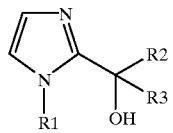

in which:
R1 is straight-chain or branched C$_1$–C$_8$-alkyl or phenyl-(CH$_2$)$_m$—;
m is zero, 1 or 2;
where the phenyl nucleus is unsubstituted or carries one to three substituents selected from the group consisting of F, Cl, CH$_3$ and CH$_3$O,
R2 and R3
are straight-chain or branched C$_1$–C$_6$-alkyl or phenyl, where the phenyl nucleus is unsubstituted or carries one to three substituents from the groups F, Cl, CH$_3$ or CH$_3$O;
or
R2 and R3
can together form a (C$_5$–C$_6$) ring, which is unsubstituted or to which phenyl rings are fused,
or of a pharmaceutically tolerable salt thereof.
9. A method of preserving or protecting organ transplants for surgical measures, comprising bringing into contact with the organ transplant an effective amount of a compound I

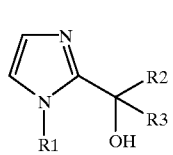

in which:
R1 is straight-chain or branched C$_1$–C$_8$-alkyl or phenyl-(CH$_2$)$_m$—;
m is zero, 1 or 2;
where the phenyl nucleus is unsubstituted or carries one to three substituents selected from the group consisting of F, Cl, CH$_3$ and CH$_3$O,
R2 and R3
are straight-chain or branched C$_1$–C$_6$-alkyl or phenyl, where the phenyl nucleus is unsubstituted or carries one to three substituents from the groups F, Cl, CH$_3$ or CH$_3$O;
or
R2 and R3
can together form a (C$_5$–C$_6$) ring, which is unsubstituted or to which phenyl rings are fused,
or of a pharmaceutically tolerable salt thereof.

* * * * *